United States Patent [19]

Murakami et al.

[11] Patent Number: 4,560,931

[45] Date of Patent: Dec. 24, 1985

[54] SELF-PROPELLED MOBILE PIPELINE INSPECTION APPARATUS AND METHOD FOR INSPECTING PIPELINES

[75] Inventors: Shinichi Murakami, Osaka; Takao Mihara, Matsubara, both of Japan

[73] Assignee: Kubota, Ltd., Osaka, Japan

[21] Appl. No.: 403,030

[22] Filed: Jul. 29, 1982

[30] Foreign Application Priority Data

Aug. 7, 1981 [JP] Japan .................................. 56-124390

[51] Int. Cl.[4] ...................... G01N 27/87; G01N 29/04; G01D 9/00; G03B 29/00
[52] U.S. Cl. ...................................... 324/220; 73/623; 346/33 P; 352/131
[58] Field of Search ................................ 324/219–221; 73/622, 623, 40.5 R; 356/241; 378/59, 60; 354/63; 346/33 P; 352/131, 132

[56] References Cited

U.S. PATENT DOCUMENTS

| | | | |
|---|---|---|---|
| 2,684,464 | 7/1954 | Hastings et al. | 324/220 |
| 3,766,775 | 10/1973 | Gunkel | 73/623 |
| 4,055,989 | 11/1977 | Henry et al. | 73/622 X |
| 4,283,628 | 8/1981 | Kulekov et al. | 378/60 |
| 4,353,257 | 10/1982 | Vrba et al. | 73/623 |
| 4,372,658 | 2/1983 | O'Connor et al. | 346/33 P X |

FOREIGN PATENT DOCUMENTS

| | | |
|---|---|---|
| 56-3427 | of 1981 | Japan . |
| 631988 | 11/1949 | United Kingdom . |
| 641657 | 8/1950 | United Kingdom . |
| 1312229 | 4/1973 | United Kingdom . |
| 1320885 | 6/1973 | United Kingdom . |
| 1488833 | 10/1977 | United Kingdom . |
| 1509696 | 5/1978 | United Kingdom . |
| 1527158 | 10/1978 | United Kingdom . |
| 1547301 | 6/1979 | United Kingdom . |
| 2064059 | 6/1981 | United Kingdom . |

OTHER PUBLICATIONS

Pipes and Pipelines International, Oct. 1981, pp. 22–27.

Primary Examiner—Gerard R. Strecker
Attorney, Agent, or Firm—Armstrong, Nikaido, Marmelstein & Kubovcik

[57]  ABSTRACT

A mobile truck 10 furnished with power source and travel drive mechanism is set in a cargo oil pipe 48 to run inside to inspect and monitor the state of the inner surface of a pipe wall by means of its built-in magnetic flaw-detecting instrument 12 and video camera 14, so that the image signals taken by the video camera 14 may be reproduced and inspected on a television receiver 30 in the monitoring stations located aboard the vessel while the inspection data signals from the magnetic flaw-detecting instrument 12 may be recorded in a recorder 20 at the same time.

11 Claims, 8 Drawing Figures

SELF-PROPELLED MOBILE PIPELINE INSPECTION APPARATUS AND METHOD FOR INSPECTING PIPELINES

BACKGROUND OF THE INVENTION

This invention relates to apparatus for inspecting the state of corrosion of fluid transfer pipes of large diameter especially cargo oil pipes used in an oil tanker.

Piping in an oil tanker poses the problems of maintenance and corrosion control.

An oil tanker typically comprises oil tanks for holding crude oil exclusively, permanent ballast tanks filled with only sea water, and tanks alternately filled with crude oil and sea water in every navigation. These tanks are connected with cargo oil pipes made of cast steel tubes of various diameters. Among those pipes, the cargo oil pipes in the main line measure about 600 to 700 mm in diameter, whereas those in the ballast line are about 400 to 500 mm in diameter.

Among factors which corrode such cargo oil pipes the main factors are chloride ions contained in seawater, inorganic sulfur compounds and organic sulfur compounds such as thioferromercaptans contained in crude oil, and sulfate ions contained in abundance in the sludge staying at the bottom of cargo oil pipes. During navigation, the cargo oil pipes are dipped in these corrosive liquids. Of these causes of corrosion, the effect of sludge is most manifest, and it is known that corrosion of a cargo oil pipe is generally initiated from the bottom part.

To inspect for corrosion, previously, ultrasonic waves or magnetic signals were applied from the outside of cargo oil pipes, and the reflected waves or eddy currents were checked for disturbance. This method, however, took much time and labor, and was difficult in complicated piping and facilities.

The simplest and most reliable method is for piping to be inspected by an inspector who gets into the cargo oil pipe and creeps along the piping to check for corrosion. The inside of the tank in a tanker is, however, extremely high or low in temperature due to thermal transfer from the ambient air or sea water, and is very narrow and thus provides a severe working environment, and, still worse, involves a risk of fatal danger due to the possibility of gas remaining in the pipe.

Besides, corrosion may be developing inside the metal of a pipe wall even if corrosion is not apparent from outside when the pipe wall is covered with a sludge deposit, in which case it is extremely difficult for the inspector, inside the pipe, to find such a concealed abnormality.

BRIEF SUMMARY OF THE INVENTION

It is an object of the invention to provide an apparatus capable of inspecting the inner surfaces of pipes such as cargo oil pipes safely and promptly by a passing mobile truck into the pipe, the mobile truck being equipped with a magnetic flaw-detecting instrument, and at the same time recording data signals from the magnetic flaw-detecting instrument at a central control unit aboard the vessel while operating the mobile truck by remote control.

Another object of the present invention is to provide an apparatus for picking up and checking the data from the mobile truck passed through a cargo oil pipe by equipping the mobile truck with a magnetic flaw-detecting instrument and an automatic recording unit and moving this mobile truck along the cargo oil pipe to record the data signals from the magnetic flaw-detecting instrument in the automatic recording unit.

Still another object of the present invention is to provide an apparatus equipped with a video camera, for monitoring a television image sent from the video camera at a monitoring station aboard the vessel while recording data signals from the magnetic flaw-detecting instrument at a central control unit aboard the vessel or in an automatic recording unit equipped on the mobile truck.

The scope of the present invention is not limited to the inspection of interior surfaces of cargo oil pipes alone, but may be extended naturally to the inspection of above-ground oil transfer pipes and buried pipes as well.

DETAILED DESCRIPTION

Figure 1:
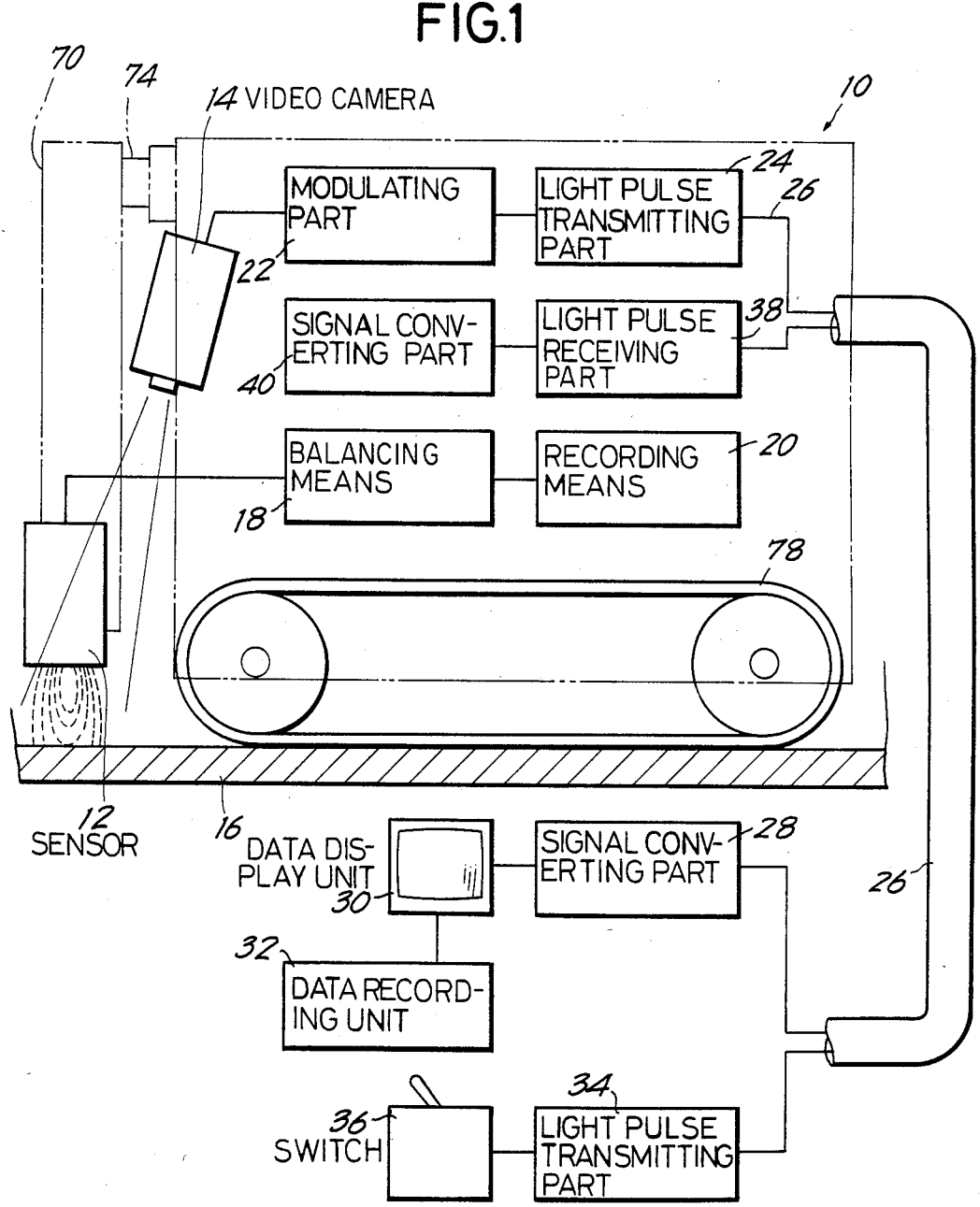
FIG. 1 is a block diagram of the signal conversion process of the magnetic flaw-detecting instrument and of the remote control.

Referring to FIG. 1, the signal conversion of the magnetic flaw-detecting instrument, video camera 14 and the signal conversion process of the remote control operation are described.

A mobile truck 10 equipped with power source and travel drive unit is furnished with a video camera 14 having a lighting device to illuminate the inspection site, a sensor 12 of a known magnetic flaw-detecting instrument and a recording device 20 to record the data sent from the sensor 12.

The sensor 12 is mounted at the lowermost end of an arm 70 which is rotatably supported on the mobile truck 10, and is rotated reciprocally in the circumferential direction of the pipe. As the rotating shaft 74 of the arm 70 is adjusted to be coaxial with the center of the pipe, the sensor 12 is maintained at a specified height from the surface of the pipe wall 16 during rotation of the arm.

The output signal from the sensor 12 is passed through a balancing means 18 composed of a bridge circuit and other circuits, and the output signal is amplified and recorded on a recording medium such as paper or magnetic tape at recording means 20 which is installed on mobile truck 10.

A current is passed through the sensor 12 to induce an eddy current in the pipe wall forming a magnetic field loop together with the oil pipe wall 16.

The truck 10 is moved on the inside surface of the cargo oil pipe while rotating the sensor 12 transversely and maintaining it at a specified height from the pipe wall.

Figure 7:
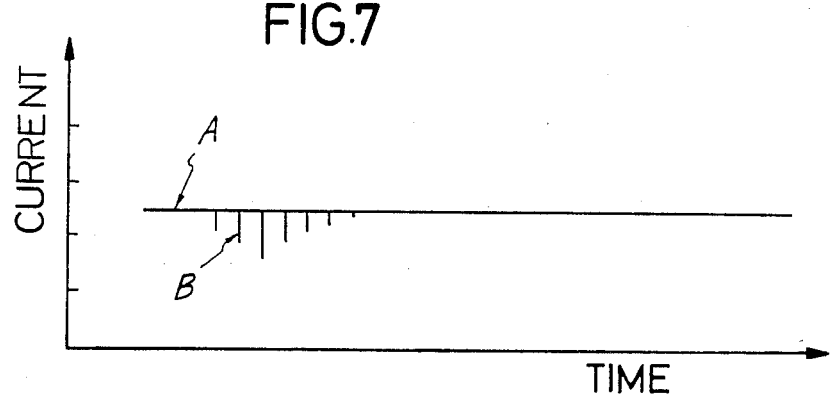
FIG. 7 is a recorded diagram of data sent from the magnetic flaw-detecting instrument.

So long as the pipe wall is in normal condition, the distance between the sensor 12 and pipe wall 16 is unchanged, and therefore current passing in the sensor 12 and producing the magnetic field loop is maintained constant as shown at A in FIG. 7.

When the pipe wall is corroded and the wall thickness is reduced or a crack is present, a disturbance appears in the magnetic field loop and current in the sensor 12. At the irregular region in the pipe wall caused by corrosion or by crack, the magnetic reluctance increases in proportion with the depth of the corrosion or crack, and therefore current passing in the sensor 12 is disturbed as shown at B in FIG. 7 at every instance when the sensor 12 traverses the irregular region on the pipe 16. Since the sensor 12 is swung transversely about four times per second, the sensor 12 passes over the irregular region very swiftly, therefore the signal B of the current appears on the recording medium almost like pulse signals. By calibrating the amperage of the output current signal to the distance of sensor 12 from the pipe wall 16 the configuration of signals of current on the recording medium indicates the shape and depth of corrosion or crack in the pipe wall. When the pipe is deformed and its cross section is not an accurate circle, the distance between the sensor 12 and pipe wall varies continuously during rotation of the arm, therefore signal A presents a wavy line or sine curve. However, the signal B indicating defects in the pipe wall is able to be distinguished clearly from the signal A because of the shape and interval of the signals. The sensor 12 is not restricted to the use of a magnetic field loop to detect corrosion or cracks by the disturbance and decrease of current passing through the sensor, but other kinds of sensors such as an ultra-sonic emitter and receiver or high frequency eddy current generator and sensor, laser, etc. are also applicable to the sensor 12 in this invention.

The condition of the surface of the pipe wall is recorded by the video camera 14. The output signal from the video camera 14 is modulated by a pulse signal in a modulating part 22. In a light-pulse transmittng part 24, flickering signals of about 100 nanoseconds duration are transmitted from a light-emitting diode, and the signals are received by a fiber cable 26 for optical communication. In the monitoring station aboard the vessel, the received light-pulse signals are converted to electrical signals by a signal converting part 28, which is finally connected to a data display unit 30 and a data recording unit 32. The state of the inspected surface is reproduced on the screen of the data display unit 30 to be monitored directly, and is recorded on magnetic tape in the data recording unit 32 at the same time.

Command signals for start, stop or retreat of the mobile truck are transmitted from the monitoring station through the fiber cable 26 for optical communication. The light pulse command signals are produce in a light pulse transmitting part 34 by flickering a light-emitting diode by on/off switching of the switch 36 at the monitoring station for each channel. The light pulse signals are received by a light pulse receiving part 38 equipped in the mobile truck 10, and a corresponding channel is selected, and signals to be fed to each channel are converted to electric currents in a signal converting part 40, so that commanded portions are operated.

Figure 2:
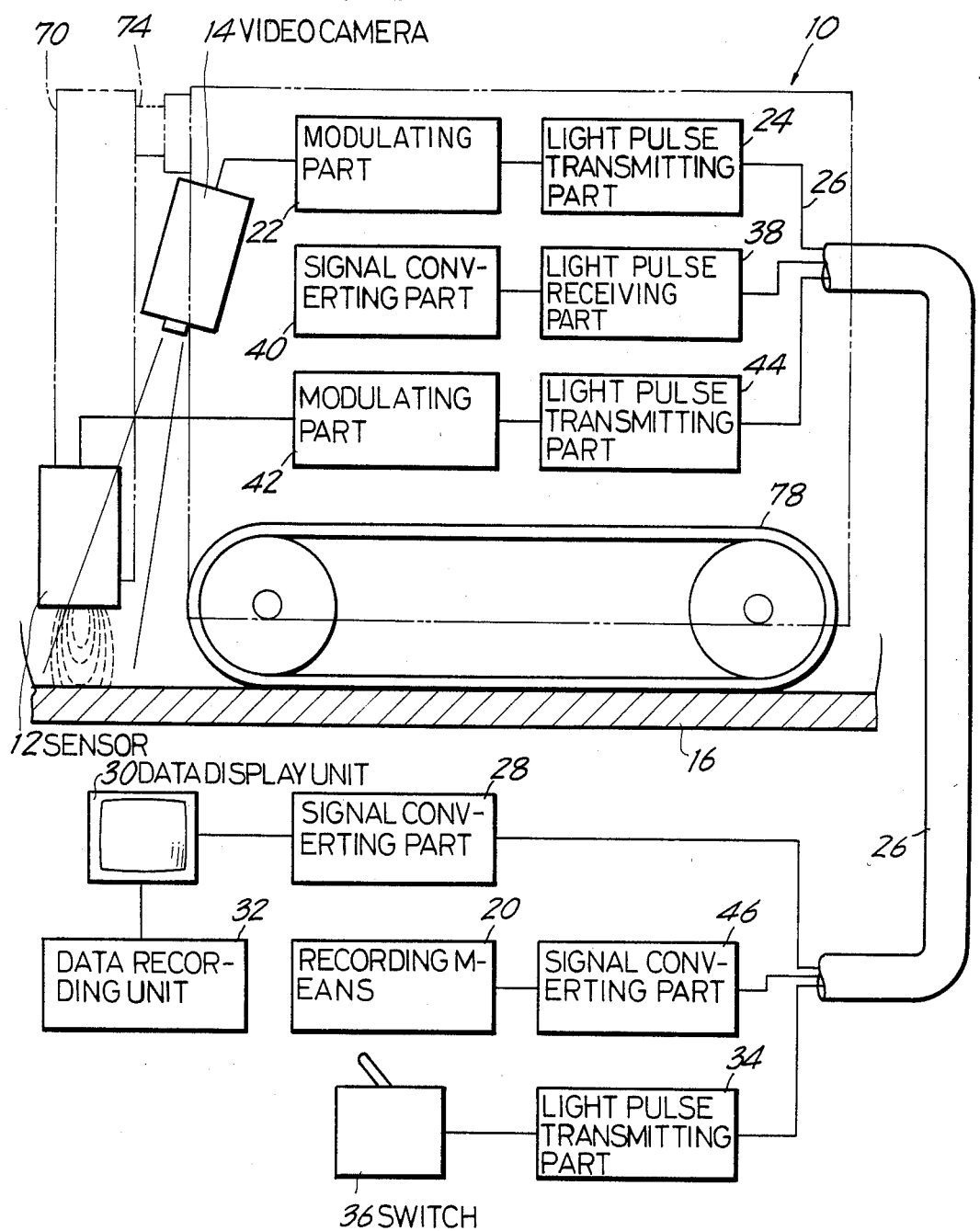
FIG. 2 is a block diagram of another embodiment of the magnetic flaw-detecting instrument.
Figure 3:
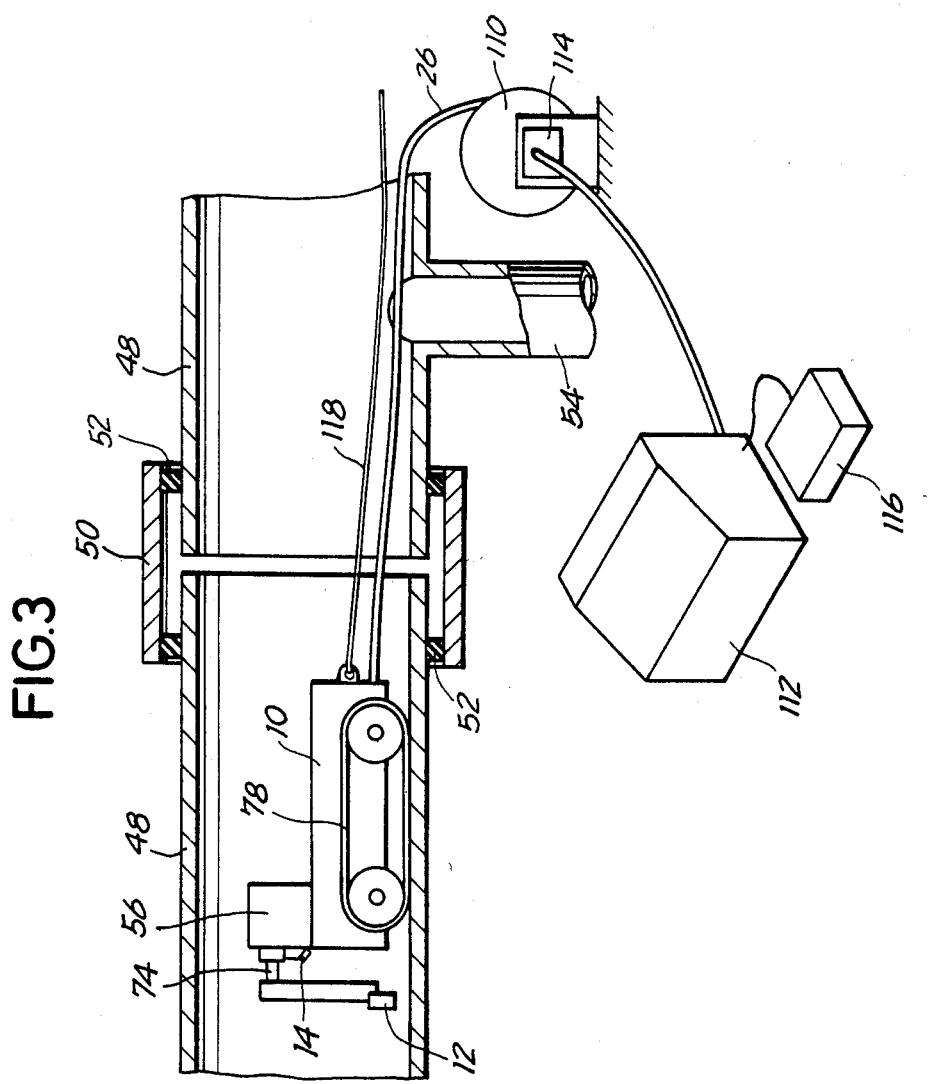
FIG. 3 is an elevation view showing the outline of an embodiment of the apparatus according to present invention.

FIG. 2 indicates another modification of this invention where recording means 20 is furnished at the monitoring station aboard the vessel. Output signals from the sensor 12 are passed through a balancing means, amplified and modulated by a pulse signal in a modulating part 42. At a light-pulse transmitting part 44, the electrical pulse signals are converted to light-pulse signals and are transmitted to a monitoring station aboard the vessel through the fiber cable 26. The light-pulse signals are converted to electric signals at the signal converting part 46 and recorded at the recording means 20 which is installed at the monitoring station. Other components having the same reference number as in the embodiment of FIG. 1 correspond with those components of FIG. 2, therefore detailed explanation about them is not provided. It should be understood as a matter of course by those skilled in the art that in both the embodiments of FIGS. 1 and 2 transmission of signals from video camera 14 to data display unit 30, from switch 36 to commanded positions on mobile truck 10, and from sensor 12 to recording means 20 (FIG. 2 only) can be achieved with electric current by using wire cable, with microwave by providing parabolic antennas on the mobile truck and at the entrance of the pipe or with electric wave (for transmitting signals from sensor 12 and switches 36 only). FIG. 3 illustrates the outline of an embodiment of this invention. Cargo oil pipes 48 are linked together by a so-called mechanical joint by means of socket 50 and packing 52 at intervals of about scores of meters.

The main line of the cargo oil pipe is provided with branch pipes 54 at several positions. Before starting inspection for corrosion and cracking of cargo oil pipes, sea water is preliminarily forced into the pipes to flush them, and then the pipes are emptied. The pipeline is opened at the branching part, bending part or joining part, and the mobile truck 10 is set in the pipe to start inspection.

The sensor 12 of the flaw-detecting instrument in the mobile truck 10 is driven by a servo-motor in the inspecting range within 60° to 360° with respect to the circumferential direction of the pipe, and is secured to a reciprocally rotating mount 56. This mount 56 is further provided with an elevating device for the sensor 12 in order to bring the reciprocally rotating shaft 74 to the center of the cargo oil pipe 48 and also to maintain the sensor 12 at the specified height from the pipe wall.

Figure 4:
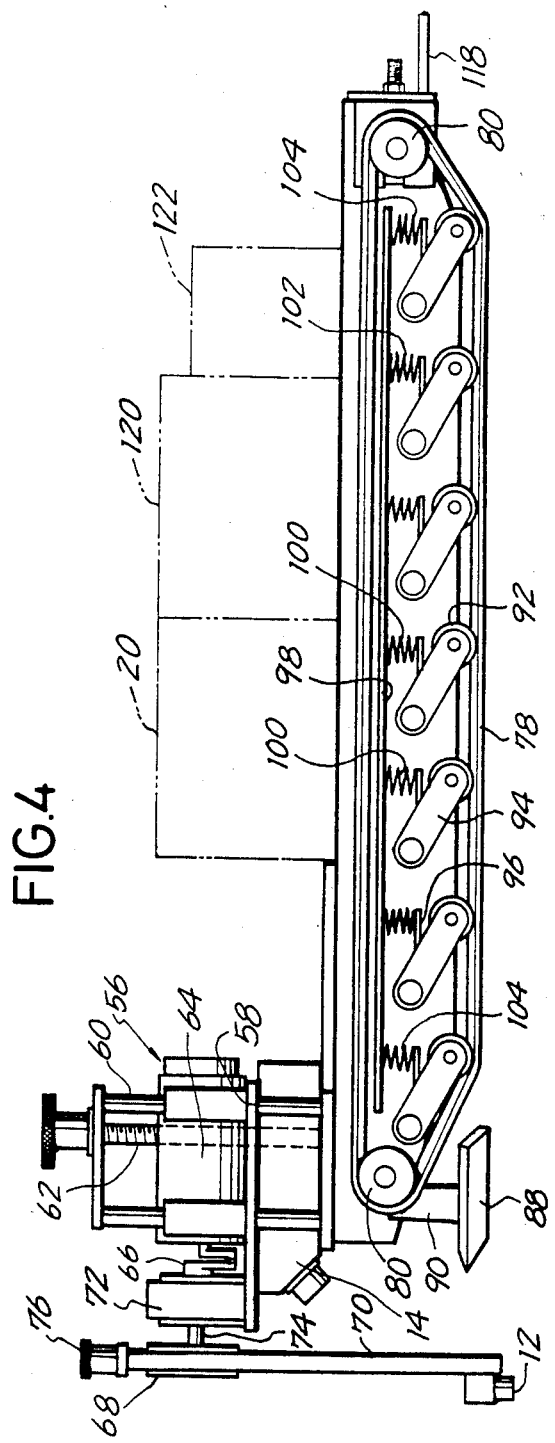
FIG. 4 is a side elevation showing the magnetic flaw-detecting instrument of the mobile truck and its surroundings.
Figure 5:
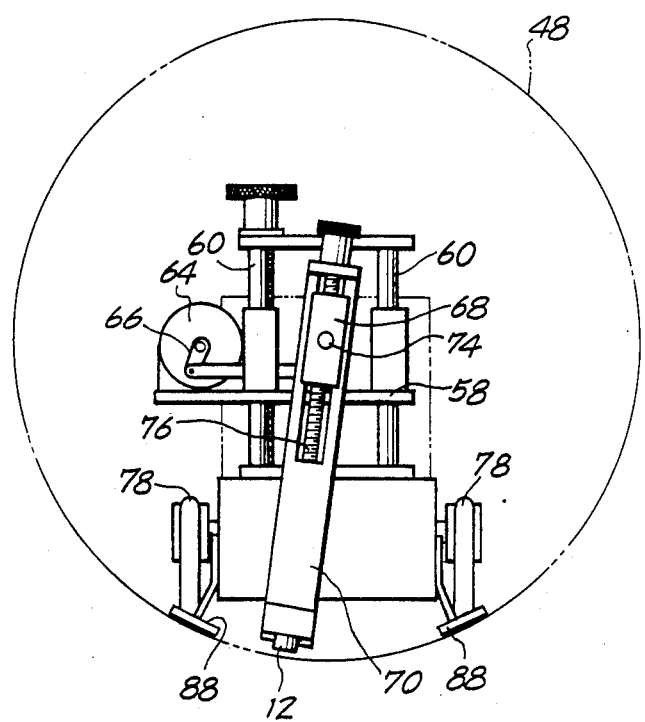
FIG. 5 is a front elevation view of the mobile truck.

As shown in FIGS. 4 and 5, the rotating mount 56 is positioned on a table 58 which is slidably secured by vertical guide posts 60 at its four corners. The table 58 also engages with a vertical and rotatable screw shaft 62. On the table 58, an electric motor 64 is provided. Drive shaft of the motor 64 is by means of crank mechanism 66 connected to a holder 68 of arm 70. The holder 68 is rotatably supported by pillow blow 72 on the table 58. At the lowermost and of the arm 70 sensor 12 is mounted, and the length of the arm 70 from the rotating shaft 74 to the sensor 12 is adjusted by operating adjusting screw 76.

The height of the table 58 is adjusted by elevating or lowering the table 58 by rotating the vertical screw shaft 62 in order to bring the rotating shaft 74 to a coaxial position with respect to the center of the cargo oil pipe 48.

The height of the sensor 12 from the pipe wall is adjusted by changing the length of arm 70 by operation of adjusting screw 76. Since the arm 70 rotates around the rotating shaft 74 which is positioned coaxial with the center of the cargo oil pipe 48, the specific height of the sensor 12 from the pipe wall is maintained during rotation of the arm 70.

Figure 6:
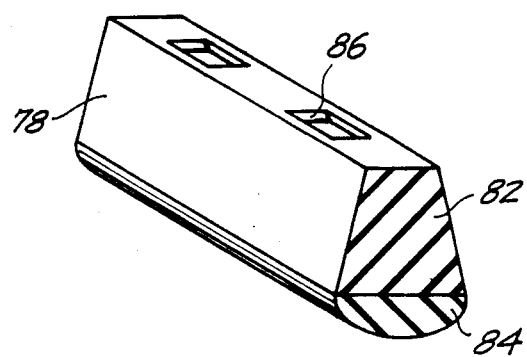
FIG. 6 is a partially cut-away perspective view of endless belt used in an embodiment of the present invention.

In the void space under the table 58, video camera 14 is installed to shoot the whole area of the pipe covered by the transverse movement of sensor 12. The moving mechanism of the mobile truck 10 has endless belt 78 furnished at both sides of the car body engaging with front and rear wheels 80, and is driven by a driving motor 122. The endless belt, as shown in FIG. 6, consists of an inner section 82 of trapezoidal shape and an outer section 84 of semicircular shape connected integrally with the inner section 82. The outer circumferential shape of the belt 78 conforms to the curvature, in the circumferential direction, of the pipe, therefore the ground contact surface area of the endless belt is sufficiently large, so that the endless belt 78 may the pipe inner surface drivingly without idling.

At the inner surface of the belt 78, pits 86 are formed at a regular interval, and on the circumference of the wheels 80, projections (not shown) are formed which engage with the pits 86 of the endless belt in order to prevent slip between the wheels 80 and belt 78.

On the extended position of the tracks of both endless belt 78, plow-shaped blades 88 are provided. The blades 88 are mounted at the lower end of bracket 90 which extend downwardly from the car body and are positioned near the forward end of the track of the endless belt 78. The blades 88 are lowered very close to the pipe wall in order to remove sludge of crude oil and other sticky deposits, which cannot be removed by forced water flushing, from the inspecting plane. The endless belts 78 may be substituted with caterpillars by using sprocket wheels instead of wheels 80.

On both sides of the car body a train of auxiliary wheels 92 are furnished which rest on the retracting side of the endless belts 78.

Figure 8:
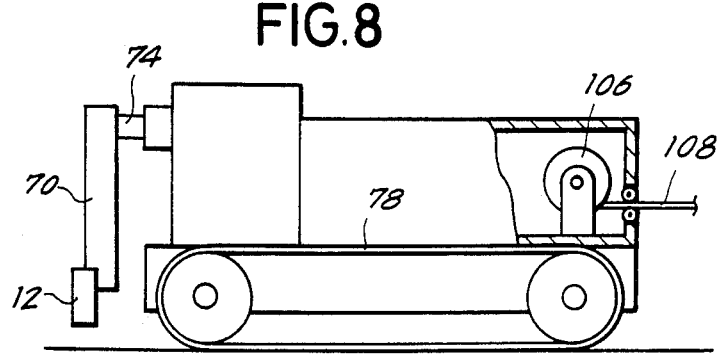
FIG. 8 is a front elevation view of the mobile truck of a further embodiment of the present invention.

Each auxiliary wheel 92 is rotatably supported at the lower end of support arm 94. The support arms 94 are rotatably fitted at their upper end to the car body and are slanted rearwardly. A stay 96 is provided to each support arm 94. Between the stay 96 of the support arm 94 and the rider 98 projecting from the car body, springs 100, 102 and 104 are inserted to elevate the car body from the ground. The springs 100 in the middle portion of the car body have the highest resilient strength, the springs 102 positioned between the middle portion and the ends have moderate strength, and the springs 104 positioned at both ends of the track are the weakest so that the springs 104 positioned at the ends absorb shock when the endless belts 78 ride over projections existing on the pipe wall, and disturbance of the signals in the recording means and video camera is eliminated. At the rear portion of the mobile truck, a rope 118 is fixed so that the truck shall be pulled back with the rope 118 to the opening of the pipe in the case of disorder in the truck. As shown in FIG. 8, a reel drum 106 of fiber cable for optical communication is provided in the rear part of the mobile truck. A fiber cable 108 of several meters to scores of meters in length is wound on the reel drum 106. The cable is unwound from the reel to drum 106 by the control from a central operation unit lest the cable should be damaged due to increased tension caused by friction between the fiber cable 26 and a pipe when the mobile truck travels a long distance from the opening of the pipeline or when the mobile truck turns a lot of bends. When the mobile truck moves backward, to the contrary, the fiber cable 108 is taken up on the reel to the original length by a power means equipped in the mobile truck.

Communication between the mobile truck and the central operation unit, and the transmissions of remote control signals depend upon cables. The cables may be commercial products of ordinary coaxial cables with plural cores, and communication via scores of channels are possible in both transmission and reception. These fiber cables guarantee stable communications within a distance of 2,000 meters.

Feeding of the cable from outside the cargo oil pipe is effected by pulling, by tractive force of the mobile truck, of the cable wound around the main reel drum 110, and its take-up is effected by driving, by remote control from the central operation unit 112, a motor (not shown) built in the main reel drum 110. Meanwhile, the main reel drum 110 is furnished with coupling 114 which is free to rotate on the drum shaft in order to prevent deflection of the cable, and the cable for extending and that for connection with equipment are joined together.

The central operation unit 112 consists of an operation panel (not shown) for the mobile truck, a display panel for data sent from the mobile truck, operation switches for main reel drum 114 and other parts. The mobile truck operation panel, by switching operations, converts control signals into optical signals by pulse light emission of a light-emitting diode, and transmits the signals to control the drive means of the mobile truck for the modes of start, stop and fast return, the mode of rotation and stop for the rotating mount of the flaw-detecting instrument, and unwinding and take-up of reel drum 106.

In order to supply the electric power necessary for traveling of mobile truck, a power line is built into the cable, and the power is fed from the central operation unit 112 to the mobile truck. In other embodiments, the necessary power may be from batteries 120 built in the mobile truck.

The data display panel (not shown) of the central operation unit 112 converts signals sent from the video camera 14 in to electric signals and displays the television image of the inner surface of the pipe wall on the display panel. The image may be recorded in video recorder 116. In the embodiment of FIG. 3 data from the sensor 12 is transfered through cable 26 and recorded in a data recording unit in the central operation unit 112.

Therefore, the inspector can monitor the television image on the display, and also investigate the recorded data after inspection, so that corroded regions and areas suspected of cracking may be investigated repeatedly.

Display of detected data is not limited to digital representation alone. By selecting the signal converter and terminal unit of the receiver built into the central operation unit 112, image display by television, analog display, or graph display may be used depending on the application.

Thus, when starting inspection of a cargo oil pipe, first the mobile truck is set in the pipe as stated above, and commands for rotation of the sensor 12 and drive of the traveling device are given from the central operation unit through remote control, thereby starting the inspection.

The cargo oil pipe may be inspected from the monitor station aboard the ship by watching the image in the display panel while referring to the piping diagram.

If a defect is found, the defective cargo oil pipe may be detached and replaced with a new pipe so that trouble may be prevented. The mobile truck, when inspecting, is moved forward at low speed until reaching the end of line, and is then returned backward at high speed to the original position, which ends one session of inspection.

For communication between the mobile truck and the central operation unit to send and to receive signals of data from the video camera 14 and from the sensor 12, and signals of command to control operating units on the mobile truck 10, electric current, micro wave signals, electric wave or light pulse signals are used, and wire cable, parabolic antenna, radio antenna of fiber cables for optical communication are used as its medium. Fiber cable for optical communication has the advantages of using light-emitting diodes of extremely low power consumption, and more than ten channels may be used in one core of fiber, and the cable itself is light in weight.

Thus, by using the method of the present invention, the inside of cargo oil pipes may be inspected, once the apparatus is set inside, by remote control through monitoring from the central operation unit mounted aboard the vessel. The inspection is not only handy and quick, but also liberated from offensive environments in the tank bottom and is quite safe.

The scope of the present invention is not limited to the descriptions and drawings given hereby, but may be applied in many different versions by any person having ordinary knowledge in this technical field within the claims of the present invention without deviating from the spirit of this invention.

What is claimed is:

1. An apparatus for inspecting the state of the inner surface of pipes, and equipped with a mobile truck having traveling means on both sides thereof for propelling the mobile truck through a pipe, said apparatus further comprising:
   a flaw-detecting sensor mounted at a lower end of a rotating arm, the sensor being adapted for sensing flaws in the pipe wall;
   a rotating mount provided on the mobile truck and connected to an upper end of the rotating arm for rotating the arm reciprocably in the circumferential direction of the pipe so as to rotate the sensor reciprocably in said circumferential direction;
   a central operation unit located outside the pipe for remotely controlling the traveling means for propulsion of the mobile truck and the rotating mount of the mobile truck for reciprocating the rotating arm, the central operation unit and the mobile truck being operably connected by a communication cable;
   a data recording unit provided at the central operation unit and operably connected to the sensor, for recording output signals produced by the sensor; and
   a video camera mounted on the mobile truck, for viewing the inner surface of a pipe at locations over which the sensor is rotated, output signals from the video camera being sent to the central operation unit by means of an optical fiber communication cable operably connecting the mobile truck and the central operation unit.

2. A pipe inspecting apparatus as defined in claim 1 wherein the flaw-detecting sensor emanates a magnetic field loop which passes into the pipe wall and induces eddy current in the pipe wall, the sensor being operable to detect disturbance of the eddy current occurring in the pipe wall when the sensor passes over corrosion or a crack in the pipe wall.

3. A pipe inspecting apparatus as defined in claim 1 wherein the flaw-detecting sensor consists of an emitter and receiver of ultra-sonic waves, for detecting the delay in the reflection of ultra-sonic waves at sites of corrosion or a crack in the pipe wall.

4. A pipe inspecting apparatus as defined in claim 1 wherein the flaw-detecting sensor comprises a generator for inducing eddy current in the pipe wall and a sensor of eddy current for detecting disturbance of eddy current occurring at sites of corrosion or a crack in the pipe.

5. A pipe inspecting apparatus as defined in claim 1 wherein data recording data unit is mounted on the mobile truck.

6. A pipe inspecting apparatus as defined in claim 1 wherein the data recording unit is provided at a monitoring station.

7. A pipe inspecting apparatus as defined in claim 1 wherein the rotating mount is provided with an adjusting means which moves the rotating shaft of the rotating arm to the coaxial position of the pipe.

8. A pipe inspecting apparatus as defined in claim 1 wherein the rotating arm is provided with adjusting means which moves the sensor along with the arm so as to establish a predetermined clearance between the sensor and the pipe wall.

9. A pipe inspecting apparatus as defined in claim 1 wherein electric power necessary for traveling of the mobile truck and sensor is taken off from batteries built in the mobile truck.

10. A pipe inspecting apparatus as defined in claim 1 wherein electric power, necessary for traveling of the mobile truck and operating video camera and sensor, is fed from the central operation unit by a feeder which is built in the communication cable.

11. A process for inspecting the state of the inner surface of pipes by sending a mobile truck into a pipe, wherein the mobile truck travels in the pipe along the length thereof, comprising:
   causing the mobile truck to travel along the pipe while reciprocating a flaw-detecting sensor carried by the mobile truck circumferentially relative to a bottom portion of the pipe wall;
   recording data obtained from the sensor as it is reciprocated;
   viewing the same portion of the pipe wall as inspected by the sensor with a video camera mounted on the mobile truck;
   communicating with the sensor and the video camera from a monitor station located remotely from the pipe;
   commanding the sensor to inspect the pipe wall, the video camera to view the pipe wall and drive means on the mobile truck to cause the mobile truck to travel in the pipe and the sensor to reciprocate, from a central operation unit in the monitor station in communication with the mobile truck.

* * * * *